United States Patent
Elghazaly et al.

(10) Patent No.: US 8,157,802 B2
(45) Date of Patent: Apr. 17, 2012

(54) INTRAMEDULLARY IMPLANT WITH LOCKING AND COMPRESSION DEVICES

(75) Inventors: Timothy M. Elghazaly, Piscataway, NJ (US); Philip H. Frank, Maplewood, NJ (US)

(73) Assignee: EBI, LLC, Parsippany, NJ (US)

( * ) Notice: Subject to any disclaimer, the term of this patent is extended or adjusted under 35 U.S.C. 154(b) by 926 days.

(21) Appl. No.: 12/117,765

(22) Filed: May 9, 2008

(65) Prior Publication Data
US 2008/0221577 A1    Sep. 11, 2008

Related U.S. Application Data

(63) Continuation-in-part of application No. 11/627,575, filed on Jan. 26, 2007.

(51) Int. Cl.
*A61B 17/72* (2006.01)

(52) U.S. Cl. .......................................... 606/64

(58) Field of Classification Search ............ 606/62–68
See application file for complete search history.

(56) References Cited

U.S. PATENT DOCUMENTS

| | | |
|---|---|---|
| 1,007,107 A | 10/1911 | Hulsmann |
| 2,068,152 A | 1/1937 | Rowe |
| 2,201,674 A | 5/1940 | Rowe et al. |
| 2,222,156 A | 11/1940 | Rowe |
| 2,725,915 A | 12/1955 | Johnson |
| 2,789,276 A | 4/1957 | Hummel |
| 2,913,031 A | 11/1959 | Mckay et al. |
| 3,308,865 A | 3/1967 | Raichelson et al. |
| 3,501,993 A | 3/1970 | Swenson |
| 3,709,218 A | 1/1973 | Halloran |
| 3,836,941 A | 9/1974 | Izraeli |
| 3,990,438 A | 11/1976 | Pritchard |
| 4,354,399 A | 10/1982 | Katayama et al. |
| 4,429,600 A | 2/1984 | Gulistan |
| 4,450,835 A | 5/1984 | Asnis et al. |
| 4,466,314 A | 8/1984 | Rich |
| 4,622,959 A | 11/1986 | Marcus |
| 4,710,075 A | 12/1987 | Davison |
| 4,733,661 A | 3/1988 | Palestrant |
| 4,756,307 A | 7/1988 | Crowninshield |

(Continued)

FOREIGN PATENT DOCUMENTS

DE    69511549 T2    3/2000

(Continued)

OTHER PUBLICATIONS

PCT International Search Report and the Written Opinion of the International Searching Authority for PCT/US2008/000568, mailed Jun. 2, 2008.

(Continued)

*Primary Examiner* — Eduardo C Robert
*Assistant Examiner* — Jerry Cumberledge
(74) *Attorney, Agent, or Firm* — Harness, Dickey

(57) ABSTRACT

An intramedullary fixation device includes an intramedullary implant having a longitudinal bore along a longitudinal axis, a two-component compression device and a two-component locking device, both devices preassembled in the longitudinal bore. The intramedullary implant includes an elongated slot and first and second apertures transversely crossing the longitudinal axis. The compression device is movable along the longitudinal axis and defines an end opening aligned with the elongated slot of the intramedullary implant. The locking device includes first and second openings aligned along the first and second apertures of the intramedullary implant.

21 Claims, 14 Drawing Sheets

U.S. PATENT DOCUMENTS

| | | | |
|---|---|---|---|
| 4,776,330 A | 10/1988 | Chapman et al. | |
| 4,827,917 A | 5/1989 | Brumfield | |
| 4,828,562 A | 5/1989 | Kenna | |
| 4,858,602 A | 8/1989 | Seidel et al. | |
| 4,875,475 A * | 10/1989 | Comte et al. | 606/64 |
| 4,895,572 A | 1/1990 | Chernoff | |
| 5,034,013 A | 7/1991 | Kyle et al. | |
| 5,041,114 A | 8/1991 | Chapman et al. | |
| 5,041,115 A | 8/1991 | Frigg et al. | |
| 5,066,296 A | 11/1991 | Chapman et al. | |
| 5,112,333 A | 5/1992 | Fixel | |
| 5,190,544 A | 3/1993 | Chapman et al. | |
| 5,295,991 A | 3/1994 | Frigg | |
| 5,383,525 A | 1/1995 | Daly et al. | |
| 5,505,734 A | 4/1996 | Caniggia et al. | |
| 5,653,709 A | 8/1997 | Frigg | |
| 5,658,287 A * | 8/1997 | Hofmann et al. | 606/63 |
| 5,690,515 A | 11/1997 | Cipolla | |
| 5,697,930 A | 12/1997 | Itoman et al. | |
| 5,704,939 A * | 1/1998 | Justin | 606/63 |
| 5,728,128 A | 3/1998 | Crickenberger et al. | |
| 5,779,705 A | 7/1998 | Matthews | |
| 5,935,127 A | 8/1999 | Border | |
| 6,004,324 A * | 12/1999 | Gahr et al. | 606/67 |
| 6,010,506 A | 1/2000 | Gosney et al. | |
| 6,019,761 A | 2/2000 | Gustilo | |
| 6,036,696 A | 3/2000 | Lambrecht et al. | |
| 6,077,267 A | 6/2000 | Huene | |
| 6,080,024 A | 6/2000 | Miller et al. | |
| 6,106,528 A | 8/2000 | Durham et al. | |
| 6,120,504 A | 9/2000 | Brumback et al. | |
| 6,168,595 B1 | 1/2001 | Durham et al. | |
| 6,214,013 B1 | 4/2001 | Lambrecht et al. | |
| 6,221,074 B1 | 4/2001 | Cole et al. | |
| 6,228,086 B1 | 5/2001 | Wahl et al. | |
| 6,296,645 B1 | 10/2001 | Hover et al. | |
| 6,402,753 B1 * | 6/2002 | Cole et al. | 606/62 |
| 6,406,477 B1 | 6/2002 | Fujiwara et al. | |
| 6,461,360 B1 | 10/2002 | Adam | |
| 6,520,969 B2 | 2/2003 | Lambrecht et al. | |
| 6,547,791 B1 | 4/2003 | Buhren et al. | |
| 6,562,042 B2 | 5/2003 | Nelson | |
| 6,565,573 B1 | 5/2003 | Ferrante et al. | |
| 6,569,165 B2 | 5/2003 | Wahl et al. | |
| 6,579,294 B2 | 6/2003 | Robioneck et al. | |
| 6,648,889 B2 | 11/2003 | Bramlet et al. | |
| 6,702,816 B2 | 3/2004 | Buhler | |
| 6,709,436 B1 | 3/2004 | Hover et al. | |
| 6,786,908 B2 | 9/2004 | Hover et al. | |
| 6,808,527 B2 | 10/2004 | Lower et al. | |
| 6,835,197 B2 | 12/2004 | Roth et al. | |
| 6,921,400 B2 | 7/2005 | Sohngen | |
| 6,926,719 B2 * | 8/2005 | Sohngen et al. | 606/64 |
| 6,932,819 B2 | 8/2005 | Wahl et al. | |
| 6,960,212 B2 | 11/2005 | Richelsoph et al. | |
| 7,018,380 B2 | 3/2006 | Cole | |
| 7,041,104 B1 | 5/2006 | Cole et al. | |
| 7,112,063 B2 | 9/2006 | Bulard et al. | |
| 7,182,765 B2 | 2/2007 | Roth et al. | |
| 7,249,949 B2 | 7/2007 | Carter | |
| 7,306,600 B2 | 12/2007 | Roth et al. | |
| 7,325,470 B2 | 2/2008 | Kay et al. | |
| 7,455,673 B2 | 11/2008 | Gotfried | |
| 7,527,627 B2 | 5/2009 | Ferrante et al. | |
| 7,763,021 B2 * | 7/2010 | Cole et al. | 606/64 |
| 2002/0133156 A1 | 9/2002 | Cole | |
| 2002/0156473 A1 | 10/2002 | Bramlet et al. | |
| 2003/0114855 A1 | 6/2003 | Wahl et al. | |
| 2003/0195515 A1 | 10/2003 | Sohngen | |
| 2004/0138663 A1 | 7/2004 | Kosashvili et al. | |
| 2004/0158252 A1 | 8/2004 | Prager et al. | |
| 2004/0260307 A1 | 12/2004 | Zander | |
| 2005/0010223 A1 | 1/2005 | Gotfried | |
| 2005/0069397 A1 * | 3/2005 | Shavit et al. | 411/457 |
| 2005/0070903 A1 | 3/2005 | Roth et al. | |
| 2005/0101958 A1 * | 5/2005 | Adam | 606/64 |
| 2005/0107790 A1 | 5/2005 | Qian | |
| 2005/0143739 A1 * | 6/2005 | Shinjo et al. | 606/62 |
| 2005/0203510 A1 | 9/2005 | Sohngen | |
| 2005/0273103 A1 | 12/2005 | Wahl et al. | |
| 2006/0111716 A1 | 5/2006 | Schlienger et al. | |
| 2006/0111717 A1 | 5/2006 | Saueressig et al. | |
| 2006/0122600 A1 | 6/2006 | Cole | |
| 2006/0149264 A1 | 7/2006 | Castaneda et al. | |
| 2006/0173457 A1 * | 8/2006 | Tornier | 606/62 |
| 2006/0200141 A1 | 9/2006 | Janna et al. | |
| 2006/0200160 A1 | 9/2006 | Border et al. | |
| 2006/0235395 A1 | 10/2006 | Frigg et al. | |
| 2007/0100343 A1 * | 5/2007 | Cole et al. | 606/67 |
| 2007/0233100 A1 | 10/2007 | Metzinger | |
| 2008/0183171 A1 | 7/2008 | Elghazaly et al. | |
| 2008/0221577 A1 | 9/2008 | Elghazaly | |
| 2008/0294164 A1 * | 11/2008 | Frank et al. | 606/64 |
| 2008/0300637 A1 | 12/2008 | Austin et al. | |
| 2009/0048600 A1 * | 2/2009 | Matityahu et al. | 606/62 |
| 2009/0318926 A1 | 12/2009 | Christie | |

FOREIGN PATENT DOCUMENTS

| | | |
|---|---|---|
| EP | 0764006 A1 | 3/1997 |
| EP | 1557131 | 7/2005 |
| ES | 2134479 T3 | 10/1999 |
| GB | 2290478 A | 1/1996 |
| WO | 9534248 A1 | 12/1995 |
| WO | WO-0143652 A | 6/2001 |
| WO | WO-03061495 | 7/2003 |
| WO | WO-03094763 | 11/2003 |
| WO | WO-2004082493 | 9/2004 |
| WO | WO-2004100810 A1 | 11/2004 |
| WO | WO-2006107222 A2 | 10/2006 |
| WO | WO-2007038560 A1 | 4/2007 |

OTHER PUBLICATIONS

PCT International Preliminary Report on Patentability (Chapter I of the Patent Cooperation Treaty) with PCT Written Opinion of the International Searching Authority for PCT/US2008/000568, mailed Aug. 6, 2009.

Halder, S.C., The Gamma Nail for Peritrochanteric Fractures, The Journal of Bone and Joint Surgery, May 1992, pp. 340-344, vol. 74-B, No. 3, 1992 British Editorial Society of Bone and Joint Surgery.

Damron, Timothy A., et al., Long Gamma Nail Stabilization of Pathologic and Impending Pathologic Femur Fractures, the University of Pennsylvania Orthopaedic Journal, 1999, pp. 13-20, vol. 12.

Synthes®, The Titanium Femoral Nail System, Solid and Cannulated Nails, Technique Guide, © 1996 Synthes (USA).

Stryker® Trauma, One Shot™ Device, Gamma® Locking Nail Instruments, Opera Tive Technique, © 2000 Stryker Corporation.

Stryker® Trauma, Gamma3™ The Compact Version of the Gamma™ Nail System, Operative Technique, Hip Fracture System, Trochanteric and Long Nails, Brochure, © 2004 Stryker, Printed in USA.

Non-Final Office Action for U.S. Appl. No. 12/117,765, mailed Mar. 17, 2011.

Non-Final Office Action for U.S. Appl. No. 12/183,142, mailed Mar. 16, 2011.

Office Action regarding European Patent Application No. 08 724 539.5-2310, dated Apr. 19, 2011.

First Office Action regarding Chinese Patent Application No. 200910137547.5, dated Jan. 26, 2011. English translation provided by Unitalen Attorneys at Law.

First Office Action regarding Chinese Patent Application No. 200880006581.2, dated Jan. 30, 2011. English translation provided by Unitalen Attorenys at Law.

Non-Final Office Action for U.S. Appl. No. 11/627,575 Mailed Dec. 21, 2011.

Second Chinese Office Action for Patent Application No. 200910137547.5 Mailed Dec. 16, 2011 (English Translation provided by Peksung Intellectual Property Ltd.).

\* cited by examiner

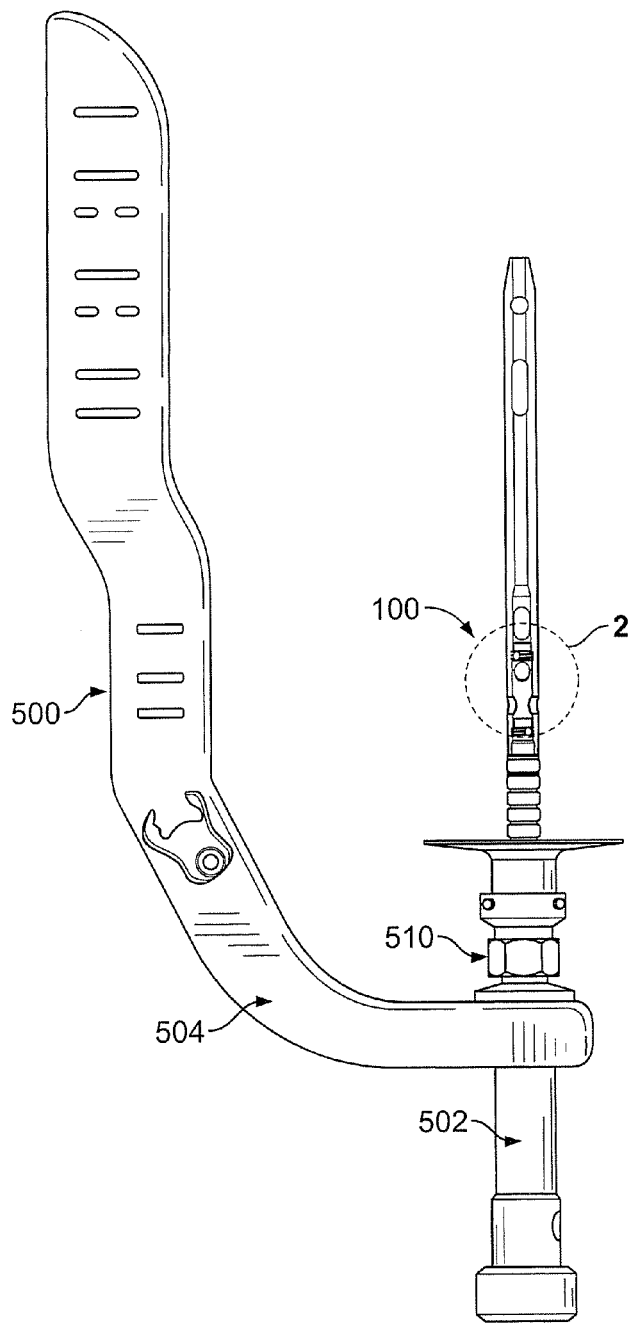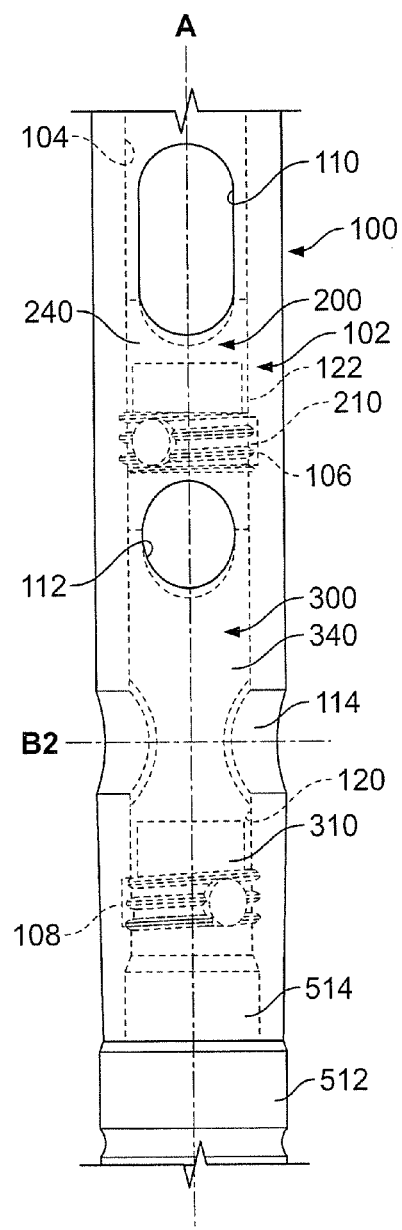
FIG. 1
FIG. 2

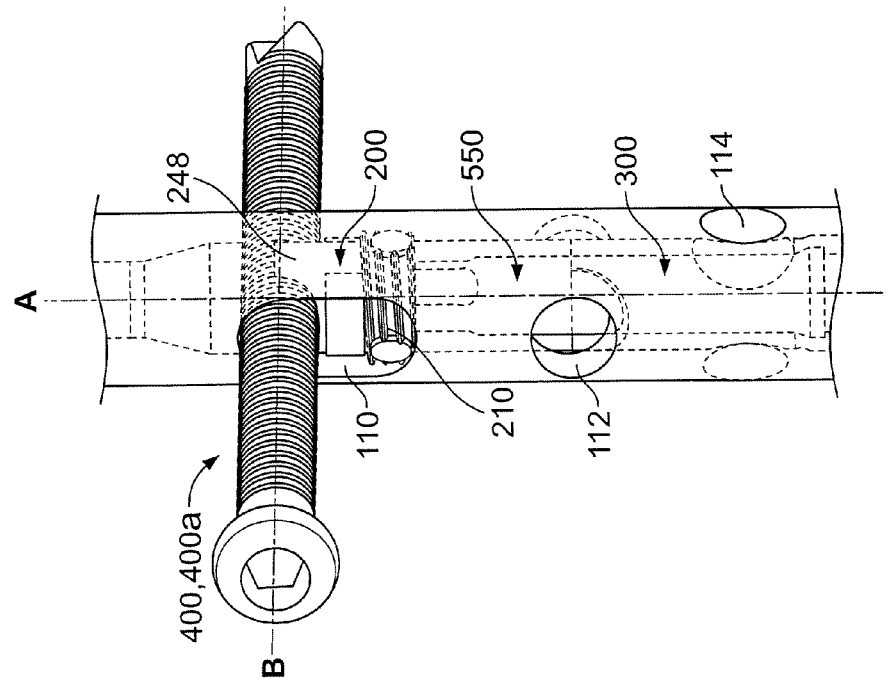
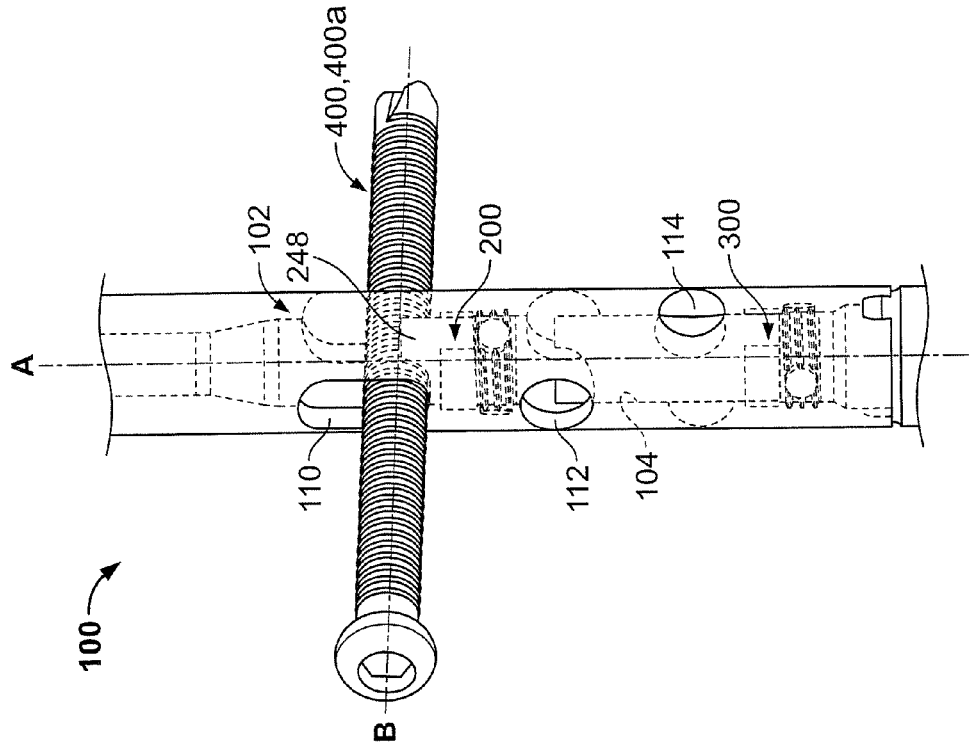

INTRAMEDULLARY IMPLANT WITH LOCKING AND COMPRESSION DEVICES

CROSS-REFERENCE TO RELATED APPLICATIONS

This application is a continuation-in-part of U.S. patent application Ser. No. 11/627,575 filed on Jan. 26, 2007. The disclosure of the above application is incorporated herein by reference.

INTRODUCTION

Different intramedullary nailing systems are known for the fixation of bone fractures, for bone reconstruction following tumor resection or other surgery or for arthrodesis operations.

The present teachings provide an intramedullary fixation device that includes separate locking and compression devices.

SUMMARY

The present teachings provide an intramedullary fixation device. In one aspect, the intramedullary fixation device includes an intramedullary implant having a longitudinal bore along a longitudinal axis, a two-component compression device and a two-component locking device. Both devices are preassembled in the longitudinal bore. The intramedullary implant includes an elongated slot and first and second apertures transversely crossing the longitudinal axis. The compression device is movable along the longitudinal axis and defines an end opening aligned with the elongated slot of the intramedullary implant. The locking device includes first and second openings aligned along the first and second apertures of the intramedullary implant.

In another aspect, the present teachings provide an intramedullary fixation device including an intramedullary implant, a compression device and a locking device. The intramedullary implant has a longitudinal bore along a longitudinal axis, and includes an elongated slot and first and second apertures transversely crossing the longitudinal axis. The compression device is preassembled in the longitudinal bore of the intramedullary implant and is movable along the longitudinal axis. The compression device includes a first component threadably coupled to the longitudinal bore of the intramedullary implant and a second component coupled to the first component, the second component having an end opening aligned with the elongated slot of the intramedullary implant. The a locking device preassembled in the longitudinal bore of the intramedullary implant, the locking device including a first component threadably coupled to the longitudinal bore of the intramedullary implant and a second component coupled to the first component, the second component including first and second openings aligned along the first and second apertures of the intramedullary implant.

In a further aspect, the present teachings provide an intramedullary fixation device that includes an intramedullary implant for ankle arthrodesis, the intramedullary implant having a longitudinal bore along a longitudinal axis, an elongated talar slot, a lateral-medial through-hole, and a posterior-anterior through-hole. The fixation device also includes a two-component compression device preassembled in the longitudinal bore of the intramedullary implant, the compression device defining an end opening corresponding to the elongated slot for receiving a talar fixation fastener transversely to the longitudinal axis of the intramedullary implant, the compression device operable to move the talar fixation fastener along the elongated slot for tibio-talar compression. The fixation device further includes a two-component locking device preassembled in the longitudinal bore of the intramedullary implant, the locking device defining a through-hole corresponding to the posterior-anterior through-hole of the intramedullary implant for receiving a first calcaneal fixation fastener, the locking device defining an end opening corresponding to the lateral-medial through-hole of the intramedullary implant for receiving a second calcaneal fixation fastener, the locking device operable to lock the first and second calcaneal fasteners in the intramedullary implant.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 1 is an elevation view of an intramedullary fixation device according to the present teachings, the fixation device shown mounted on a targeting instrument;

FIG. 2 is an elevated view of Detail D of FIG. 1;

FIG. 3 is a perspective view of a detail of an intramedullary fixation device according to the present teachings, the fixation device shown with a compression device in a disengaged position relative to a fixation fastener;

FIG. 4 is a perspective view of a detail of the fixation device of FIG. 3, the fixation device shown with the compression device in an engaged position relative to the fixation fastener;

DESCRIPTION OF VARIOUS ASPECTS

The following description is merely exemplary in nature and is in no way intended to limit the invention, its application, or uses. For example, although the present teachings are illustrated for exemplary procedures for ankle arthrodesis, the present teachings can be used for fracture reduction and other fixation procedures involving long bones, including the femur, the tibia, the forearm, the humerus, or any bone that has an intramedullary canal. It will be understood that general surgical procedures are outlined only as needed to illustrate the devices and methods provided by the present teachings, while detailed descriptions of standard and known procedures and instruments are omitted for simplicity.

Figure 6:
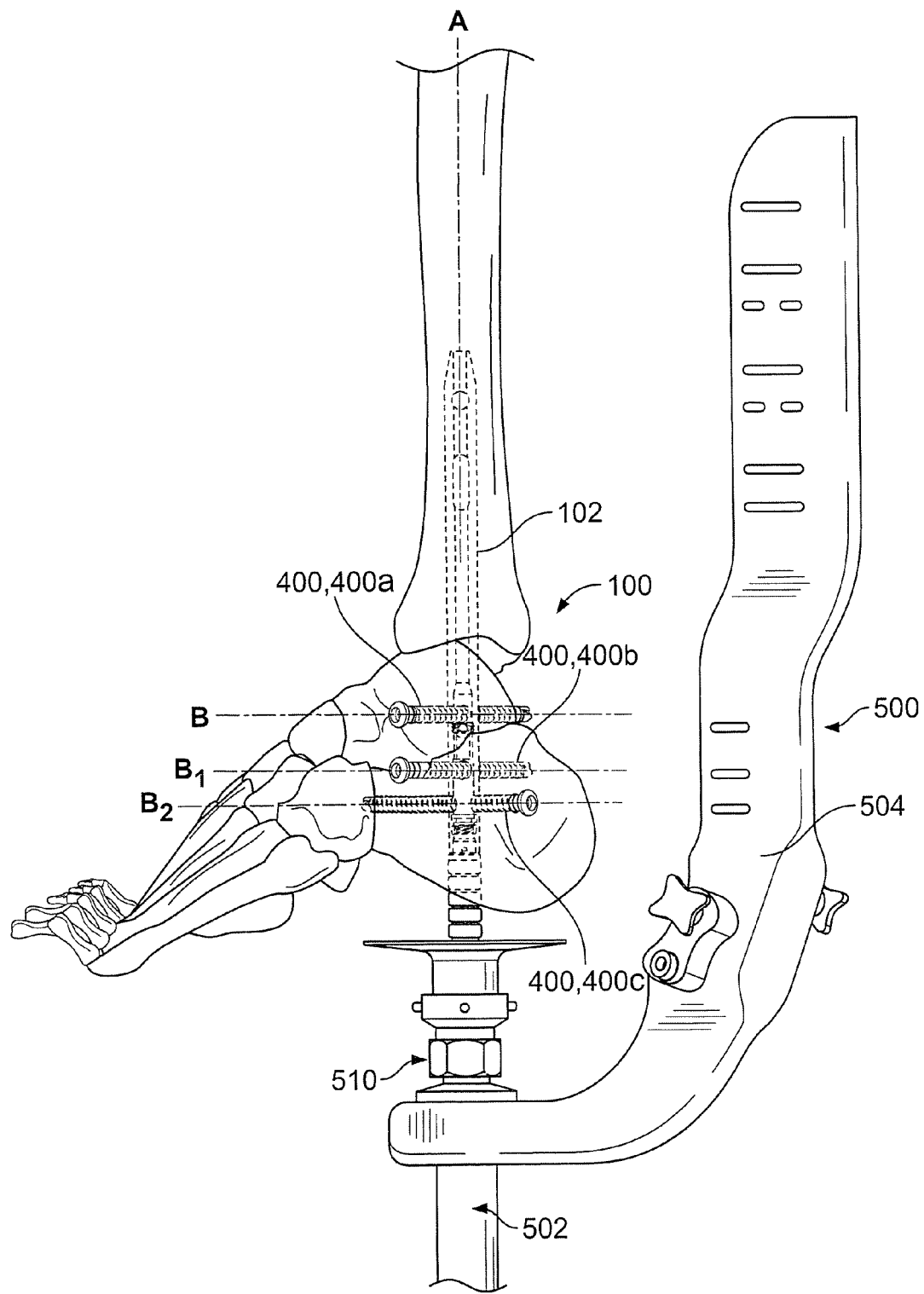
FIG. 6 is an environmental perspective view an intramedullary fixation device according to the present teachings, the fixation device shown implanted for ankle arthrodesis and coupled to a targeting instrument.

Referring to FIGS. 1 and 2, an exemplary fixation device 100 according to the present teachings is shown mounted on a targeting instrument 500. The fixation device 100 can include an elongated intramedullary (IM) implant or nail 102 having a longitudinal bore 104 along a longitudinal axis A, a compression device 200, and a locking device 300. Both the compression device 200 and the locking device 300 can be pre-assembled inside the longitudinal bore 104 of the IM implant 102. The compression device 200 and the locking device 300 can operate independently of each other and can be used with various fixation fasteners 400. The compression device 200 can be used, for example, with a compression fixation fastener 400a to provide compression of a fracture line and/or move bone segments toward one another. The locking device 300 can engage one or more locking fixation fasteners 400b, 400c and lock them to the IM implant 102, as shown in FIG. 6 in an exemplary ankle arthrodesis procedure. As illustrated, the fixation fasteners 400 can be threaded.

Referring to FIGS. 1, 2 and 6, the targeting instrument 500 can include a longitudinal shaft 502, a curved targeting arm 504 rotatably coupled to the shaft 502, and an external compression nut 510 mounted on the shaft 502. The targeting instrument 500 can include a nose or tip 512 lockingly coupled to the IM implant 102 using a connecting bolt or other connecting fastener 514. Turning the compression nut 510 by one turn can provide talo-calcaneal compression of an amount of about 1 mm, for example.

Figure 7:
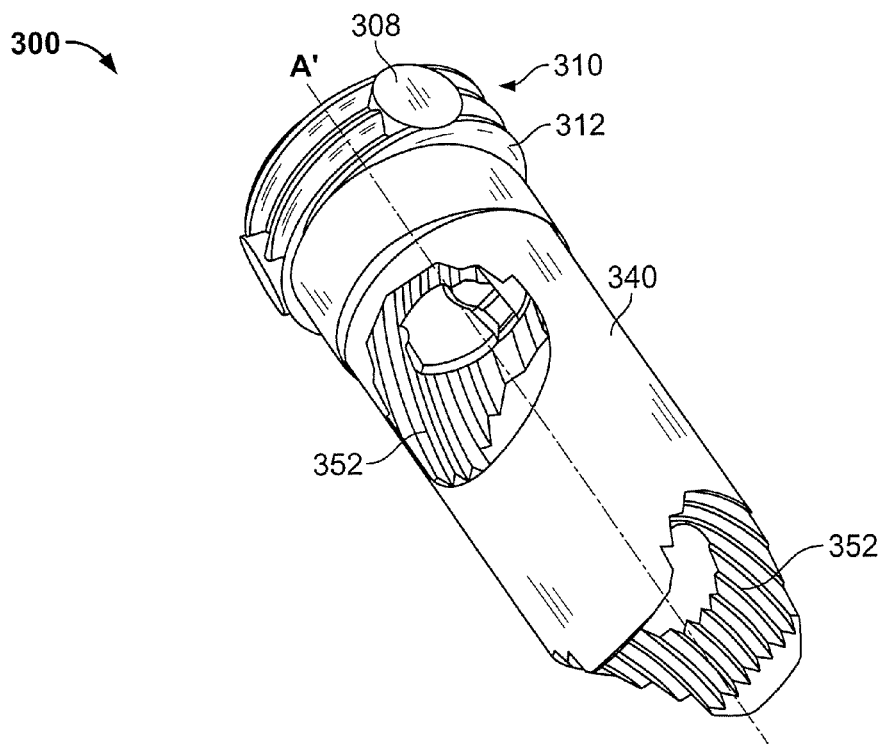
FIGS. 7 and 7A are perspective views of a locking device for an intramedullary fixation device according to the present teachings.
Figure 7A:
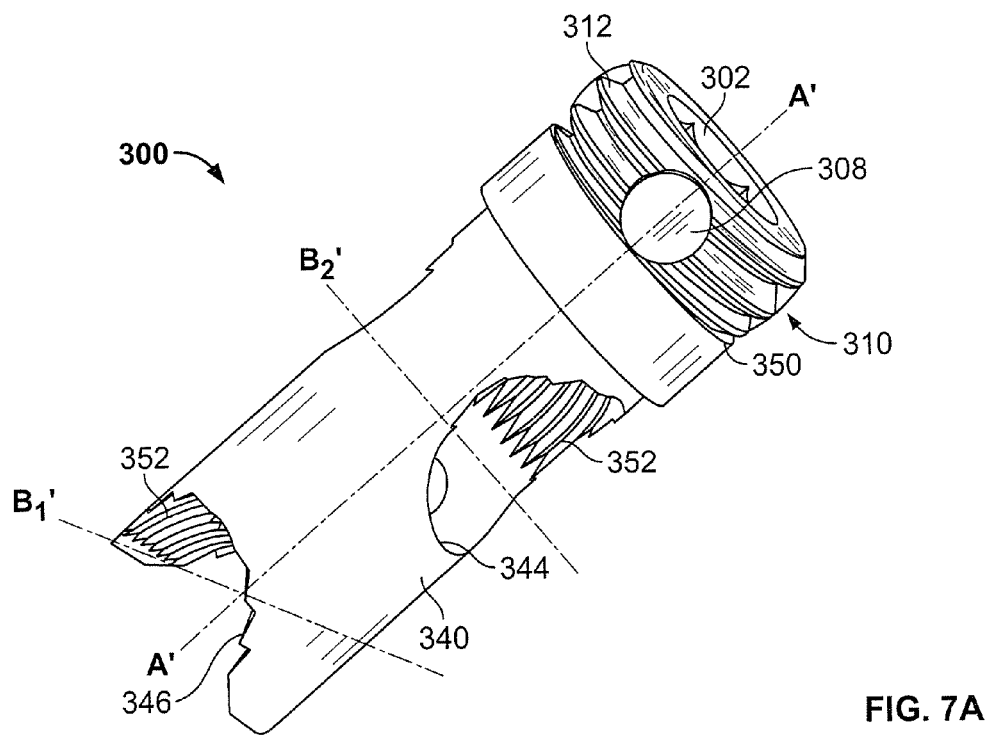
Figure 7B:
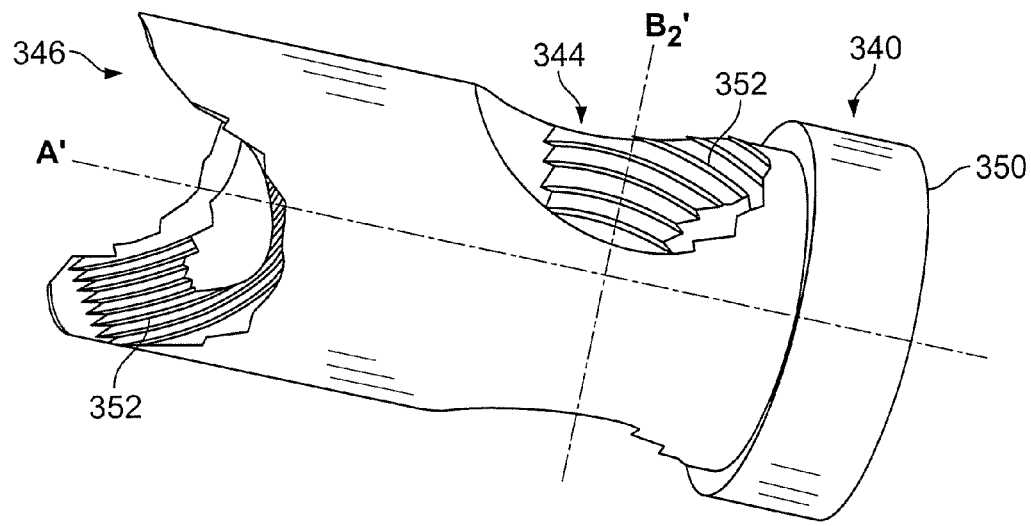
FIGS. 7B and 7C are perspective views of a first component of the locking device of FIG. 7.
Figure 7C:
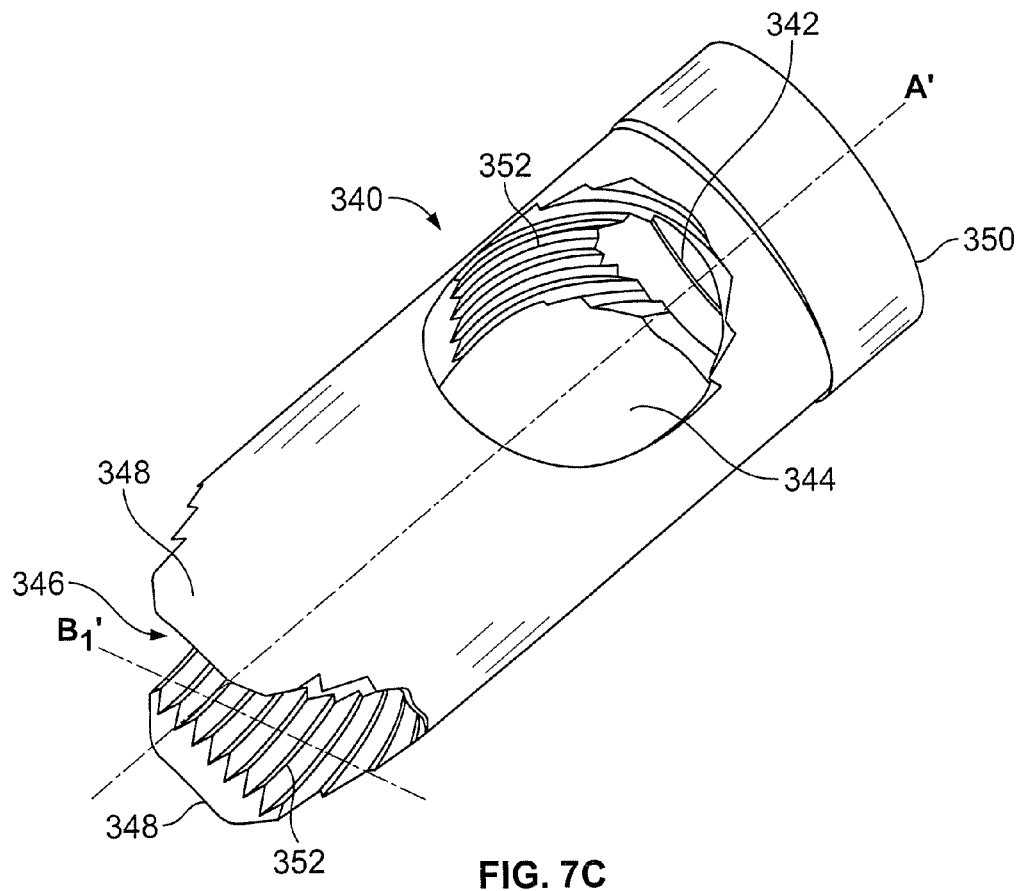
Figure 7D:
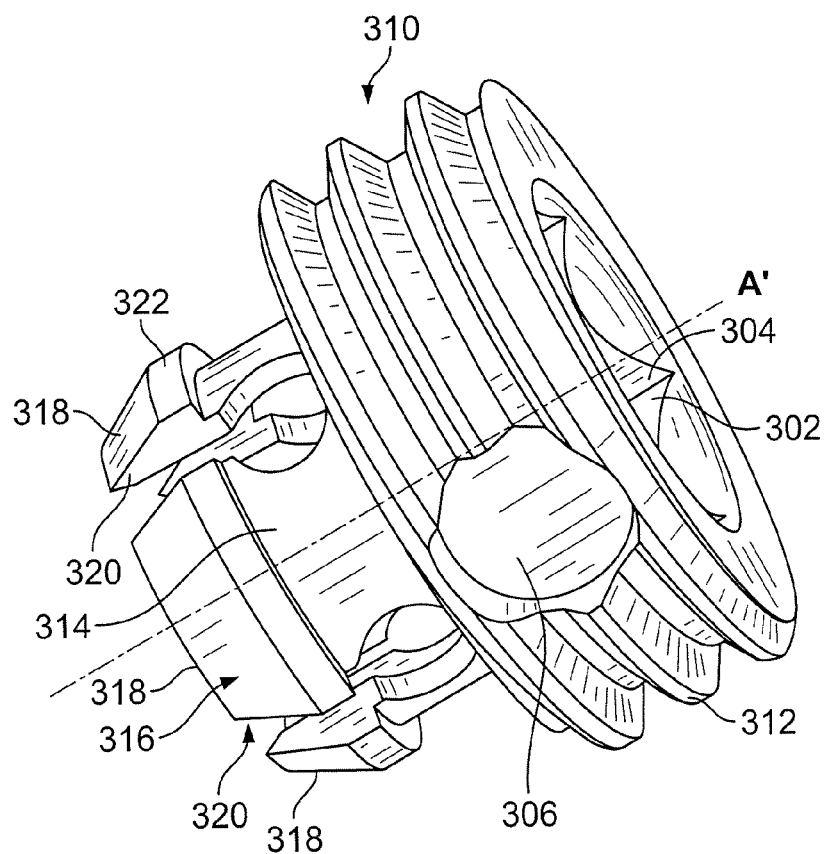
FIGS. 7D and 7E are perspective views of a second component of the locking device of FIG. 7.
Figure 7E:
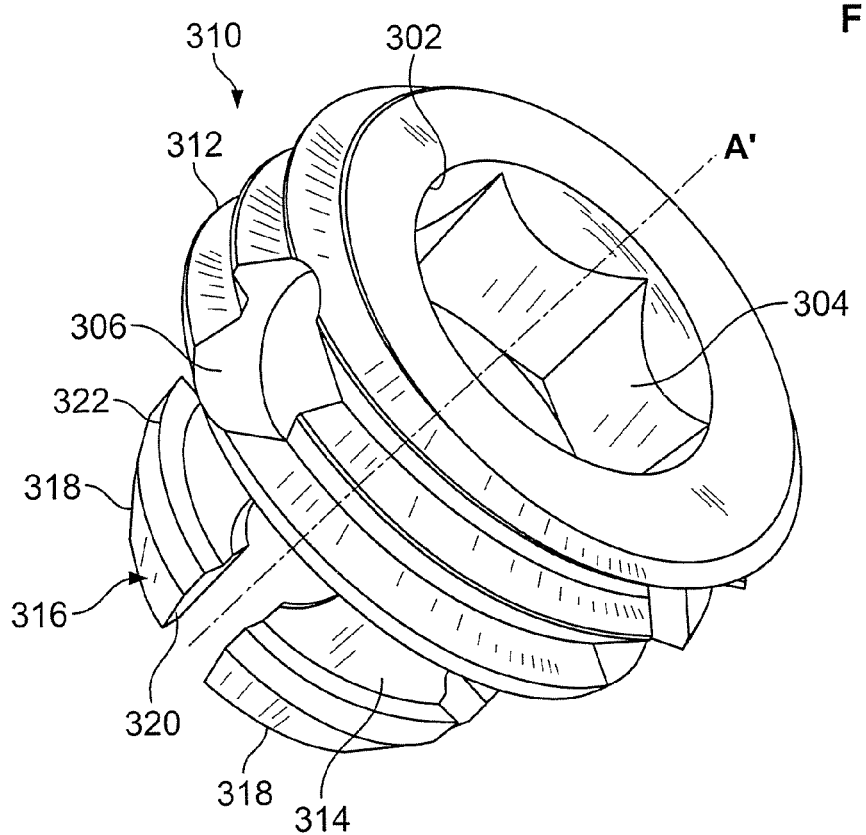
Figure 7G:
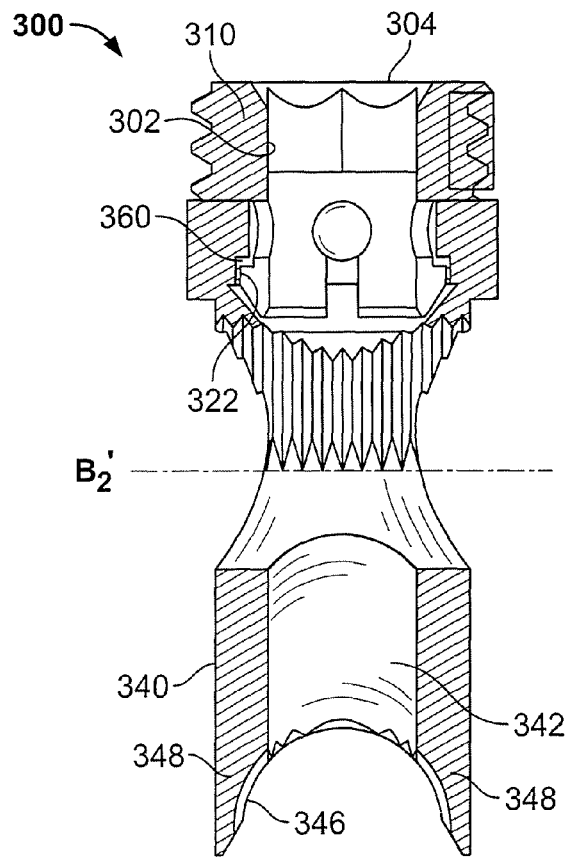
FIG. 7G is a sectional view of the longing device of FIG. 7F taken along line 7G-7G.
Figure 7F:
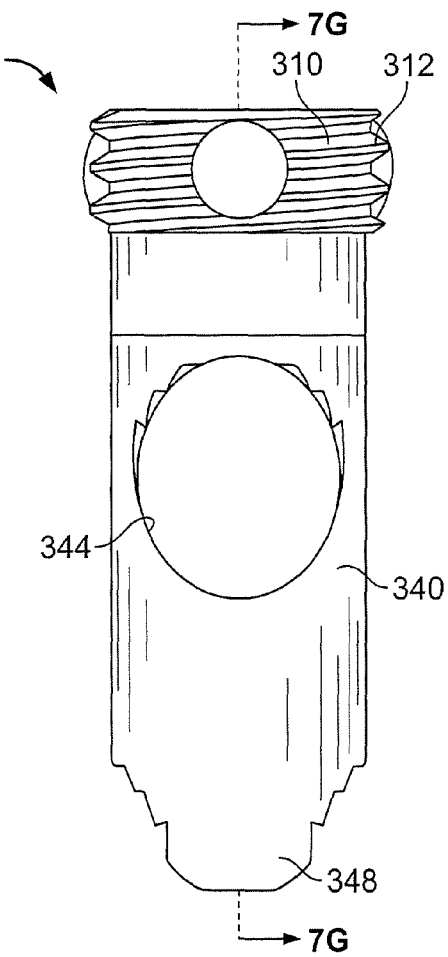
FIG. 7F is an elevated side view of the locking device of FIG. 7.
Figure 8:
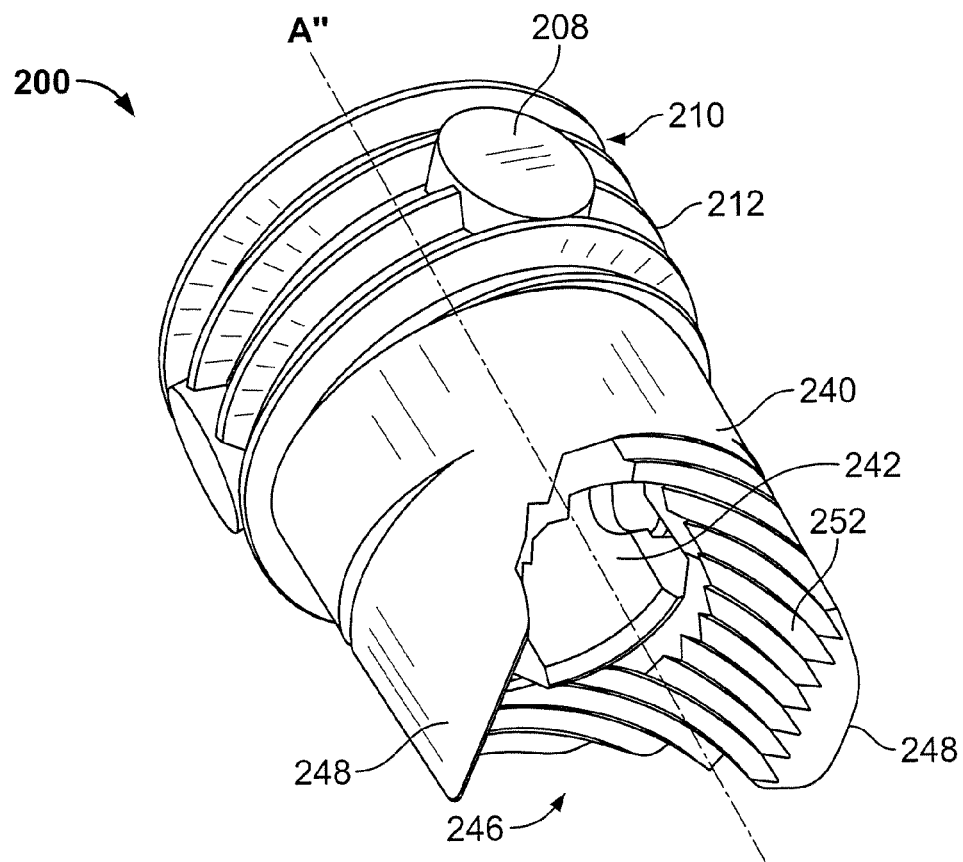
FIG. 8 is a perspective view of a compression device according to the present teachings.
Figure 8B:
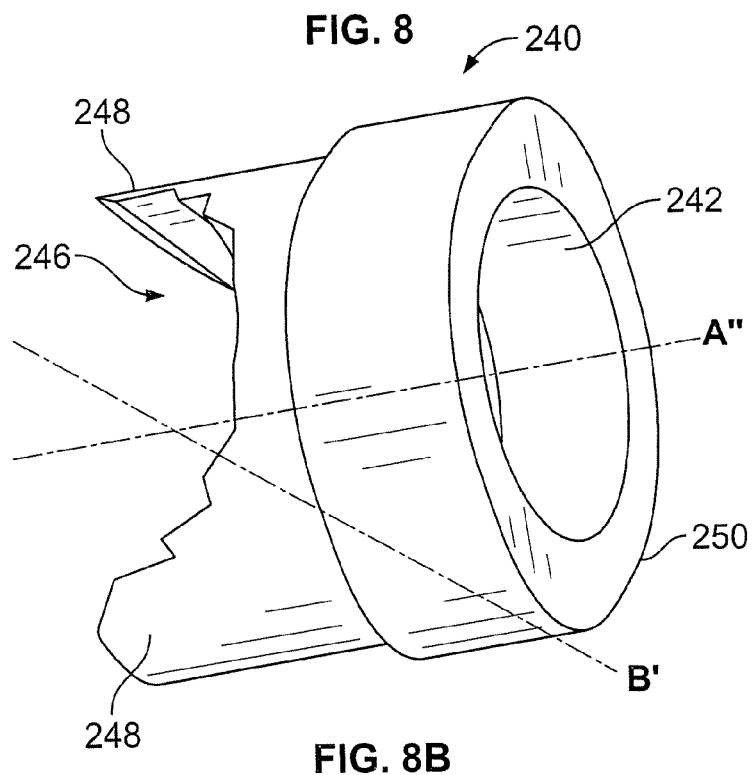
FIG. 8B is a perspective view of a first component of the compression device of FIG. 8.
Figure 8A:
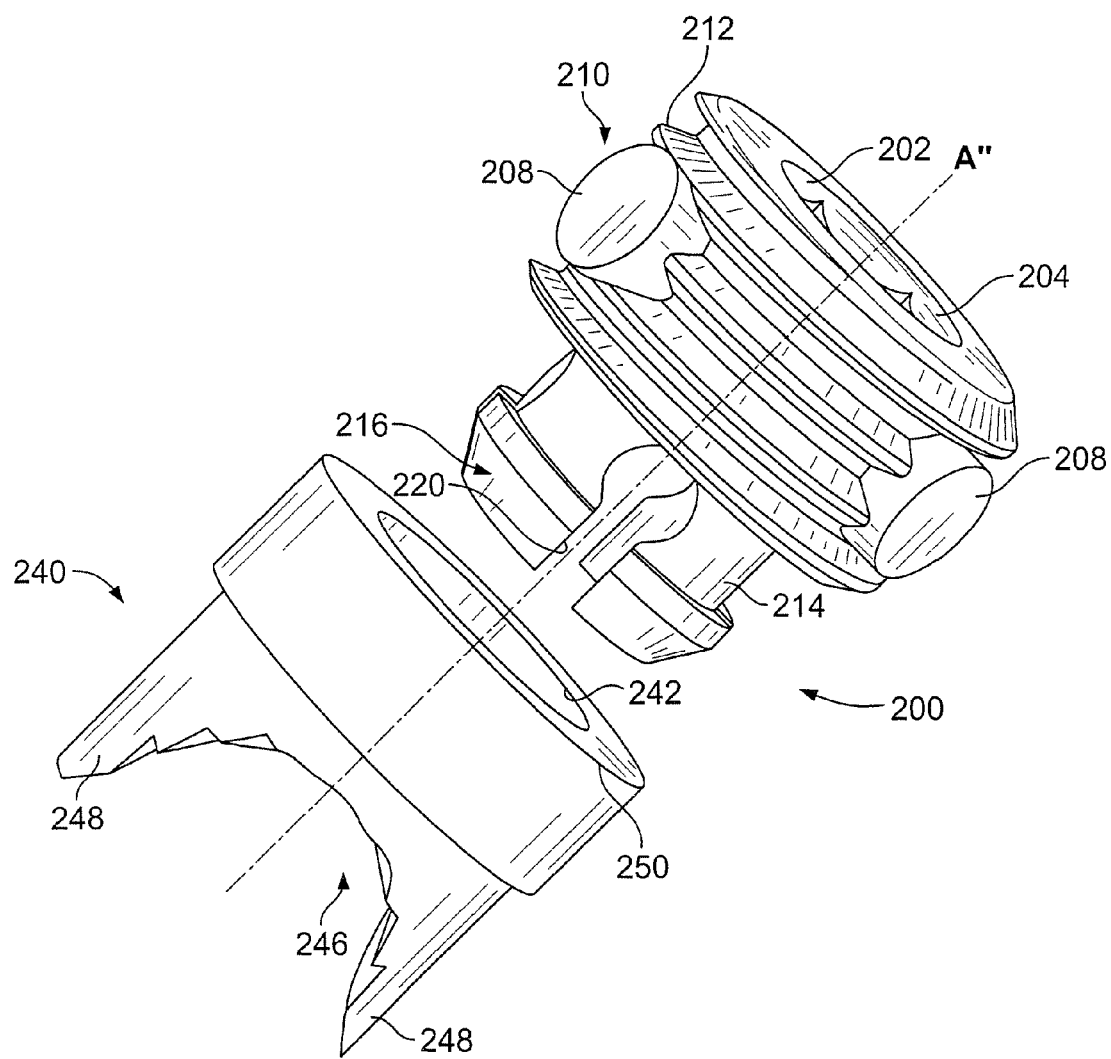
FIG. 8A is an exploded view of the compression device of FIG. 8.
Figure 8C:
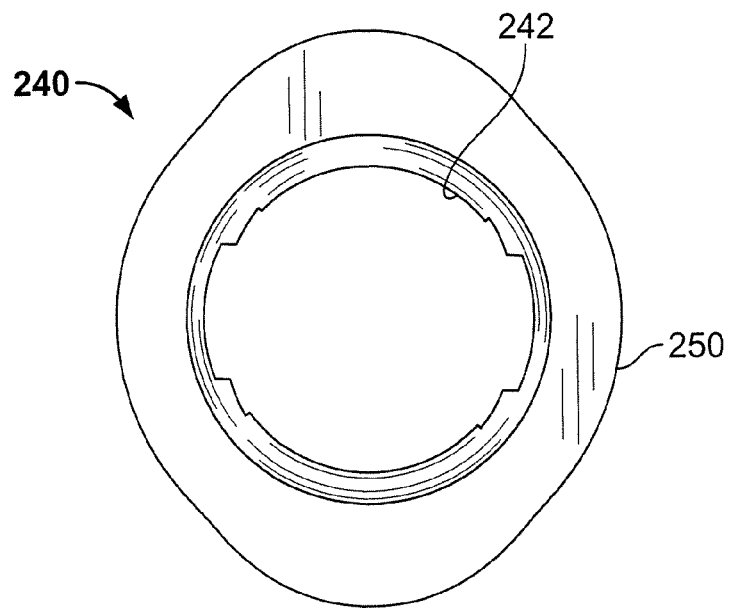
FIG. 8C is an end view of the first component of FIG. 8B.
Figure 8D:
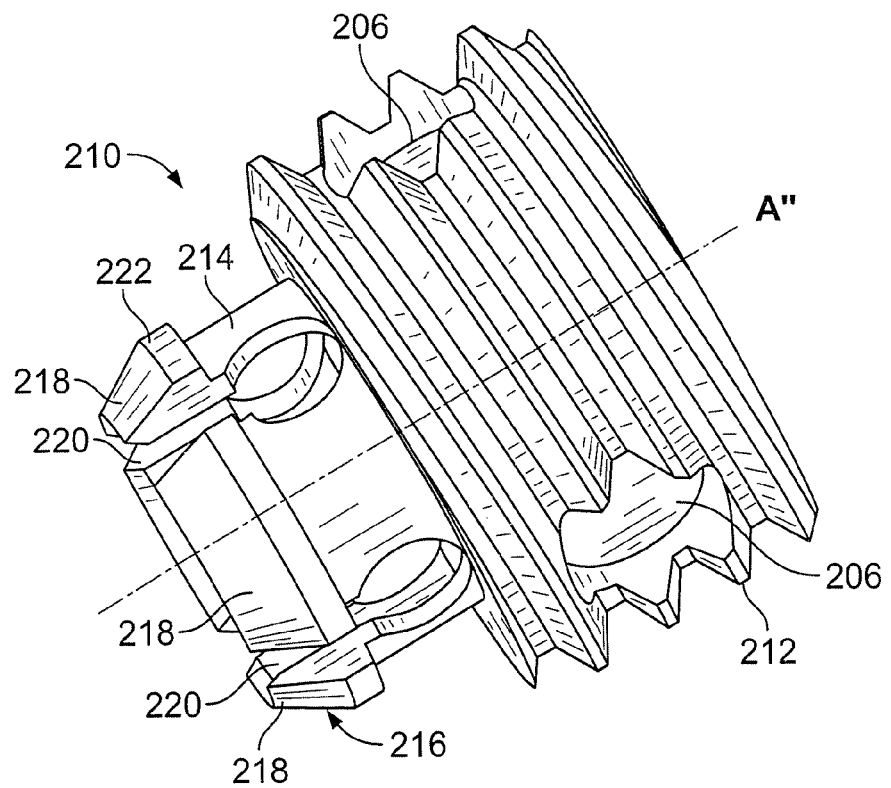
FIGS. 8D and 8E are perspective views of a second component of the compression device of FIG. 8.
Figure 8E:
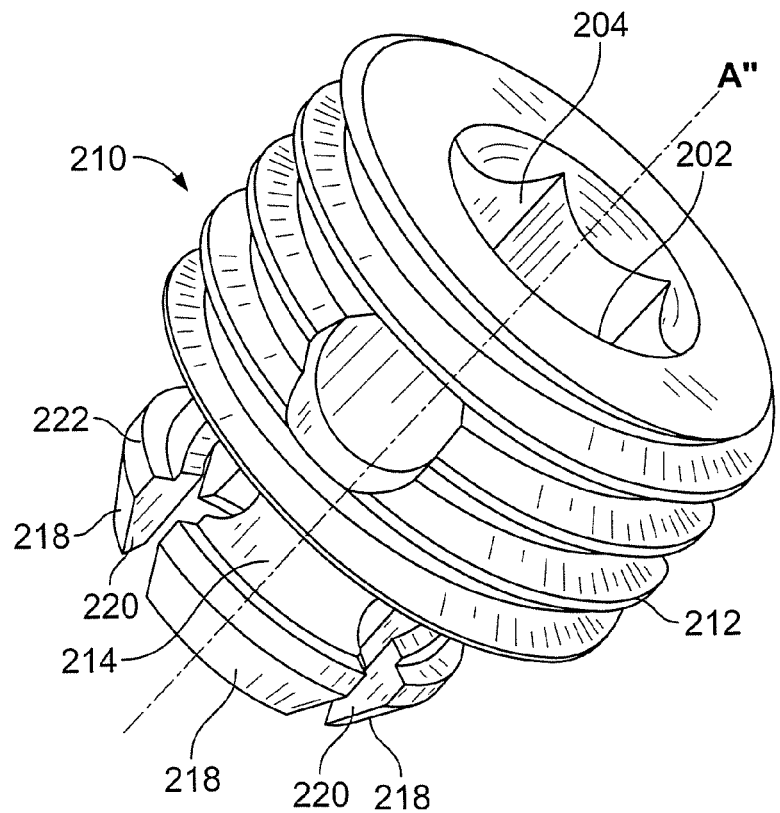
Figure 8F:
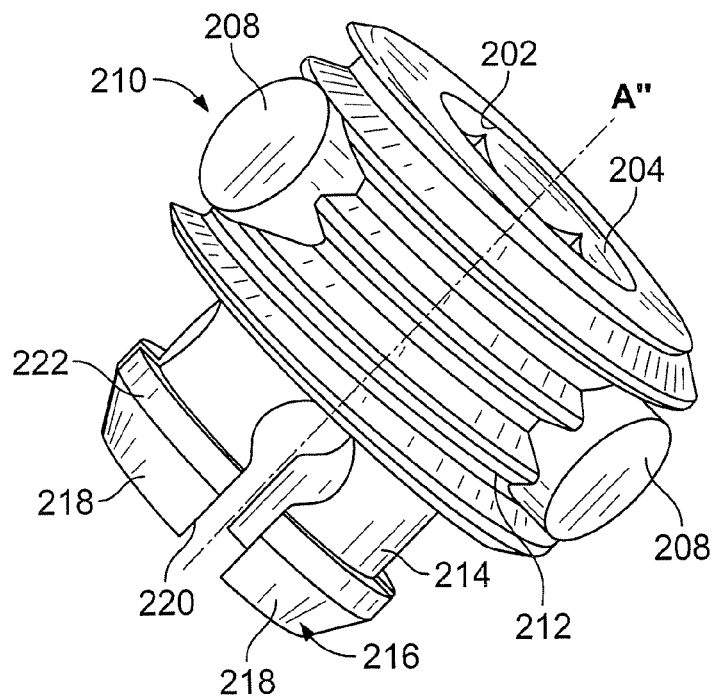
FIG. 8F is a perspective view of a second component of the compression device of FIG. 8.
Figure 8G:
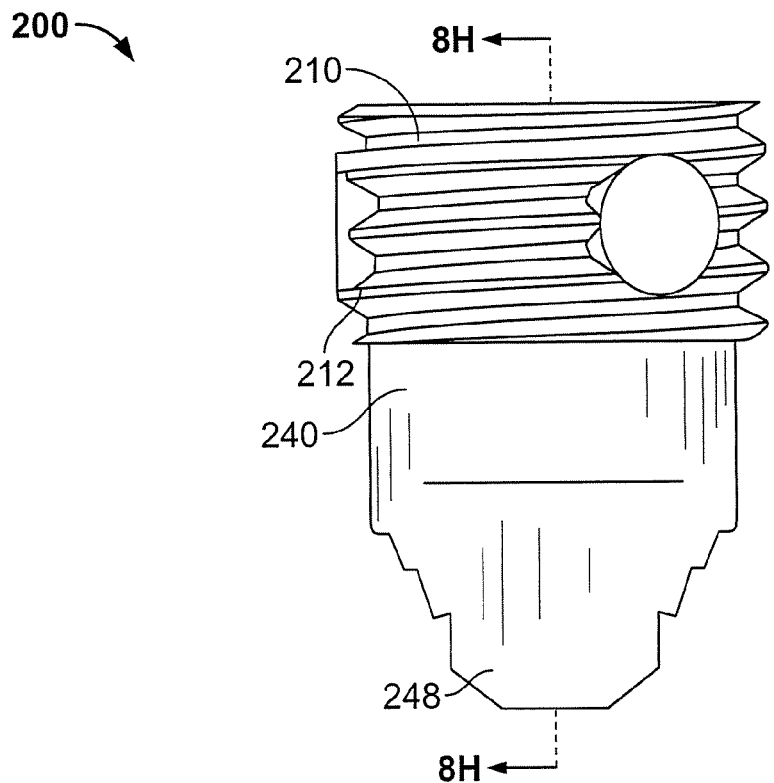
FIG. 8G is an elevated side view of the compression device of FIG. 8.
Figure 8H:
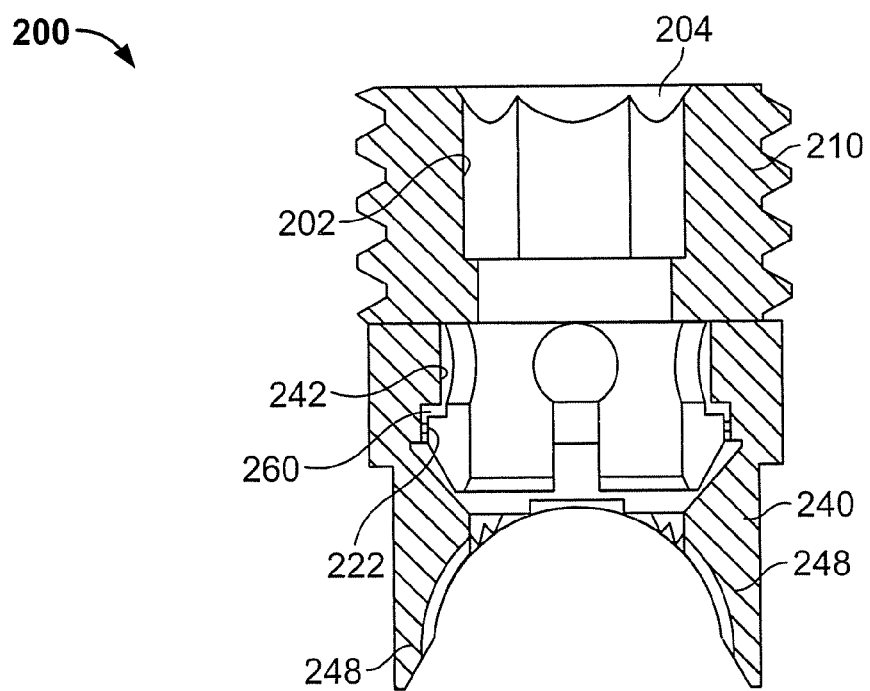
FIG. 8H is a sectional view of the compression device of FIG. 8G taken along line 8H-8H.

Referring to FIGS. 7-7G, the locking device 300 can include first and second internally cannulated components 310, 340, which can be coupled to one another by a snap-fit arrangement or other type of connection. Similarly, and referring to FIGS. 8-8H, the compression device 200 can include first and second internally cannulated components 210, 240, which can be coupled to one another by a snap-fit arrangement or other type of connection. Each of the first components 210, 310 can include a threaded portion with external threads 212, 312, respectively, for threadably engaging corresponding internally threaded portions 106, 108 of the bore 104 of the IM implant 102, as shown in FIG. 2.

Referring to FIGS. 2, 6, 10A and 10B, the IM implant 102 can have a distal portion 103 and a proximal portion 105. The distal portion 103 generally extends over the length shown in FIG. 2, which corresponds to the Detail D of FIG. 1. The distal portion 103 of the IM implant 102 can define an elongated through-slot 110, a first through-aperture 112 and a second through-aperture 114. The slot 110 can be elongated in the direction of the longitudinal axis A, and can cross transversely the longitudinal bore 104 of the IM implant 102 along an axis B, which is substantially perpendicular to the longitudinal axis A. The first aperture 112 can also cross transversely the longitudinal bore 104 of the IM implant along an axis B1. The axes B and B1 can be substantially parallel or have different orientations depending ion the application. The second aperture 114 can also cross transversely the longitudinal bore 104 of the IM implant 102 along an axis B2 which can be substantially orthogonal to axes A and B1.

For an ankle arthrodesis procedure, the slot 110 can be oriented and located for receiving a fixation fastener 400 in a talar position (talar or compression fixation fastener 400a), as illustrated in FIG. 6 in reference to an exemplary ankle arthrodesis procedure. Similarly, the first aperture 112 of the IM implant 102 can be oriented and positioned for receiving a fixation fastener 400 (calcaneal or locking fixation fastener 400b) along the lateral-medial direction corresponding to the axis B1 in the calcaneal position. The second aperture 114 can be oriented and positioned for receiving a fixation fastener 400 (calcaneal or locking fixation fastener 400c) along the anterior-posterior direction corresponding to the axis B2 in the calcaneal position. It will be appreciated that the proximal portion 105 of the IM implant 102 can also include various slots and openings for receiving other or additional fixation fasteners 400. The fixation fasteners 400 can include portion with threading 402.

Referring to FIGS. 7-7C, and 8-8B, the second components 240 and 340 of the compression and locking devices 200, 300 include corresponding openings for accommodating various fixation fasteners 400 for the talar and calcaneal positions, as discussed above.

Specifically, the second component 340 of the locking device 300 can include a longitudinal bore 342 along a longitudinal axis A' and a through-aperture or bore 344 transversely intersecting the longitudinal bore 342 along an axis B2'. The second component 340 of the locking device 300 can also an end opening 346 extending along an axis B1' and defined between two opposing end extensions 348 of the second component 340 of the locking device 300. When the locking device 300 is received within the longitudinal bore 104 of the IM implant 102, axes A', B1' and B2' align with the corresponding axes A, B1, and B2 of the IM implant 102. Accordingly, the first and second apertures 112, 114 of the IM implant substantially align with the end opening 346 and transverse aperture 344 respectively of the locking device 300.

Figure 9A:
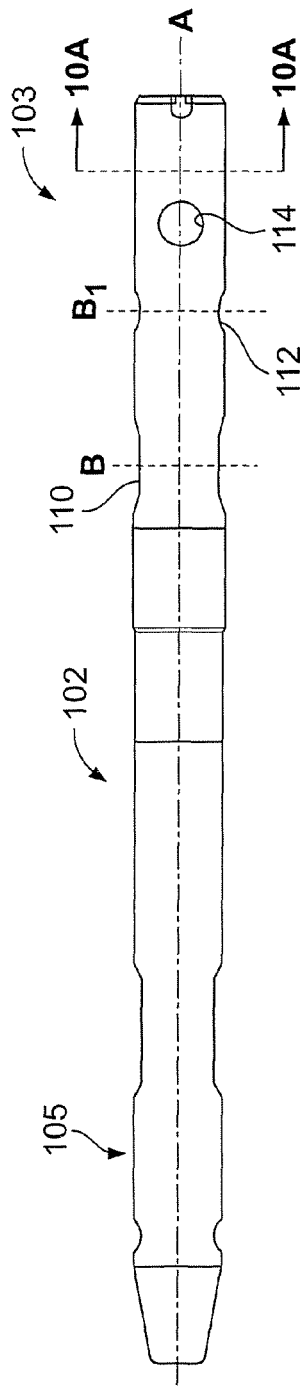
FIG. 9A is a first side view of an intramedullary implant according to the present teachings.
Figure 10A:
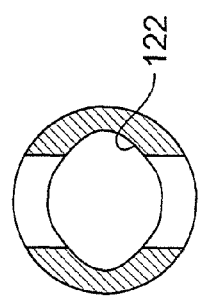
FIG. 10A is a sectional view of the intramedullary implant of FIG. 9A taken along line 10A-10A.

To maintain proper orientation between the locking device 300 and the IM implant 102 for accommodating the fixation fasteners 400, the second component 340 can be keyed to the IM implant 102. Referring to FIGS. 9A and 10A, the portion of the longitudinal bore 104 of the IM implant 102 that receives the second component 340 of the locking device 300, along section 10A-10A of FIG. 9A, for example, can be shaped to have an inner wall having a closed periphery 120 in the form of a non-circular, elongated curve, such as an ellipse or oval or other elongated shape, as shown in FIG. 10A. The second component 340 of the locking device 300 can have an outer periphery 350 of a shape substantially matching the shape of the periphery 120 of the corresponding portion of the longitudinal bore 104 of the IM implant, such that the locking device 300 can be received into the bore 104 of the IM implant in a keyed manner and maintain an orientation that aligns the corresponding openings of the locking device 300 and the IM implant 102, as discussed above. Further, inner surface portions of the end opening 346 and transverse aperture 344 of the second components 340 of the locking device 300 can include threads or ridges or other similar formations 352 for engaging and meshing with the threading 402 of the corresponding fixation fasteners 400.

Referring to FIGS. 8, 8B, 8C, 9B and 10B, the second component 240 of the compression device 200 can include a longitudinal bore 242 along a longitudinal axis A", and an end opening 246 extending about an axis B' and defined between two opposing end extensions 248 of the second component 240 of the compression device 200. When the compression device 200 is received within the longitudinal bore 104 of the IM implant 102, axes A" and B' align with the corresponding axes A and B of the IM implant 102. Accordingly, the slot 110 of the IM implant substantially aligns with the end opening 246 of the compression device 200. Further, an inner surface portion of the end opening 246 can include threads or ridges or other similar formations 252 for engaging and meshing with the threading 402 of the corresponding fixation fasteners 400.

Figure 9B:
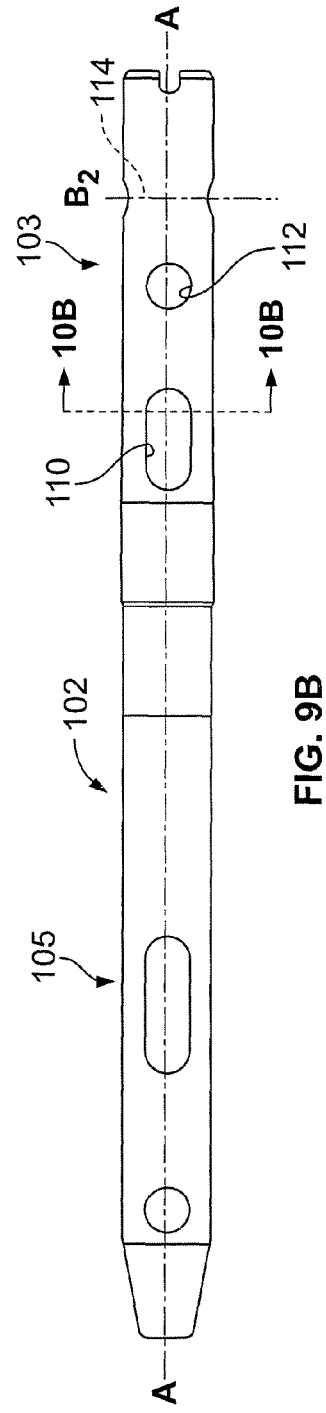
FIG. 9B is a second side view of an intramedullary implant according to the present teachings.
Figure 10B:
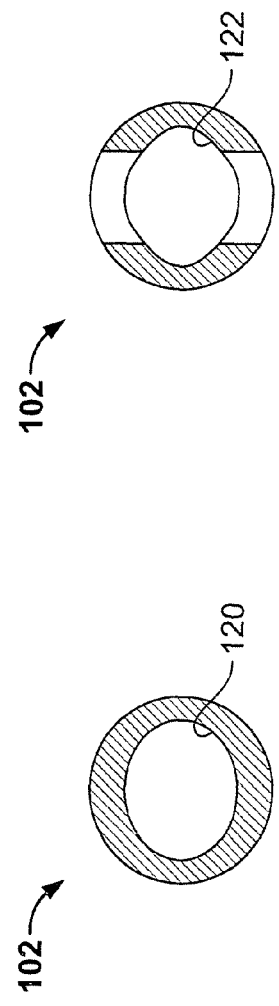
FIG. 10B is a sectional view of the intramedullary implant of FIG. 9B taken along line 10B-10B.

To maintain proper orientation between the compression device 200 and the IM implant 102 for accommodating a corresponding fixation fastener 400a through the slot 110, the second component 240 can be keyed to the IM implant 102. Referring to FIGS. 9B and 10B, the portion of the longitudinal bore 104 of the IM implant 102 that receives the second component 240 of the compression device 200, along section 10B-10B of FIG. 9B, for example, can be shaped to have an inner wall having a closed periphery 122 in the form of a non-circular curve, as shown in FIG. 10A. The second component 240 of the compression device 200 can have an outer periphery 250 of a shape substantially matching the shape of the periphery 122 of a corresponding portion of the longitudinal bore 104 of the IM implant, such that the compression device 200 can be received into the bore 104 of the IM implant in a keyed manner and maintain an orientation that aligns the end opening 246 of the compression device 200 and the slot 110 of the IM implant 102, as discussed above.

The periphery 122 that receives the second component 240 of the compression device 200 can be sized and shaped to fit into the periphery 120 that receives the second component 340 of the locking device 300, such that the second component 240 of the compression device 200 can pass through the periphery 120 of the portion of the bore 104 of the IM implant 102 that will hold the second component 340 of the locking device 300.

Referring to FIGS. 7D, 7E, 8D and 8E, the first components 310, 210 of the locking and compression devices 300, 200 can include generally similar features, and are also described in detail in co-pending U.S. patent application Ser. No. 11/627,575 filed on Jan. 26, 2007, the disclosure of which is incorporated by reference herein. It will be appreciated, however, that the size and shape of these components or portions thereof can be different. The first components 210, 310 allow the surgeon to engage/disengage the corresponding compression and locking devices 200, 300 in situ within the intramedullary implant 102, and with the intramedullary implant 102 implanted, because the first components 210, 310 can be threadably engaged with the inner threaded portions 106, 108 of the IM implant, as shown in FIG. 2.

Each of the first components 210, 310, can include a longitudinal bore 202, 302 along corresponding longitudinal axes A" and A', an unthreaded cylindrical portion 214, 314, and a distal flexible or resilient portion 216, 316, respectively. Each resilient portion 216, 316 can be defined by a plurality of legs 218, 318 extending from the unthreaded portion 214, 314 and separated by slots 220, 320, respectively. Each resilient portion 216, 316 can also define a step or flange 222, 322 that can be retained into a groove 260, 360 of the corresponding second component 240, 340, for example, when the resilient portion 216, 316 is snap-fitted into the longitudinal bore 242, 342 of the corresponding second component 240, 340, as shown in FIGS. 8G-8H, and 7F-7G, respectively.

Each first component 210, 310 of the respective compression and locking devices 200, 300 can also include a driver engagement formation 204, 304 in a proximal portion of the corresponding longitudinal bore 202, 302 for engaging a corresponding compression or locking driver 550. A compression driver 550 for engaging the compressing device 200 is illustrated in FIG. 4. The compression driver 550 can be, for example, a hex wrench specifically sized to pass through the locking device 300 to reach the compression device 200. In one aspect, the driver 550 can be flexible.

Each of the first components 210, 310 can also include holes or other openings 206, 306 that interrupt the external threads 212, 312. The openings 206, 306 can be plugged with thread locks 208, 308 for preventing further engaging or disengaging movement between the first components 210, 310 and the intramedullary implant 102, thereby securing the position of the corresponding second components 240, 340 relative to the intramedullary implant 102 and the fixation fasteners 400. The thread locks 208, 308 can be made of polyethylene, for example. In one aspect, the first component 210, 310 can be made of polyethylene. See, for example, FIG. 8F.

An exemplary procedure in relation to ankle arthrodesis is illustrated in FIGS. 2-6. FIG. 2 shows the exemplary fixation device 100 with the locking device 300 and the compression device 200 pre-assembled into the longitudinal bore 104 of the IM implant 102. Referring to FIG. 3, a talar fixation fastener 400a can be inserted through the longitudinal slot 110 of the IM implant 102 along the axis B. Referring to FIG. 4, a compression driver 550, sized or adapted for the compression device 200, can be inserted through the IM implant 102 and through the locking device 300 and engage the driver engagement formation 204 of the first component 210 of the compression device 200. Rotating the driver 550 can move the talar fixation fastener 400a along the slot 110 from a proximal end to a distal end of the slot 110 in the direction of axis A until the talar fixation fastener 400a is held in compression between the end extensions 248 of the compression device 200. An amount of internal apposition or compression of about 7 mm can be for example, achieved.

Figure 5:
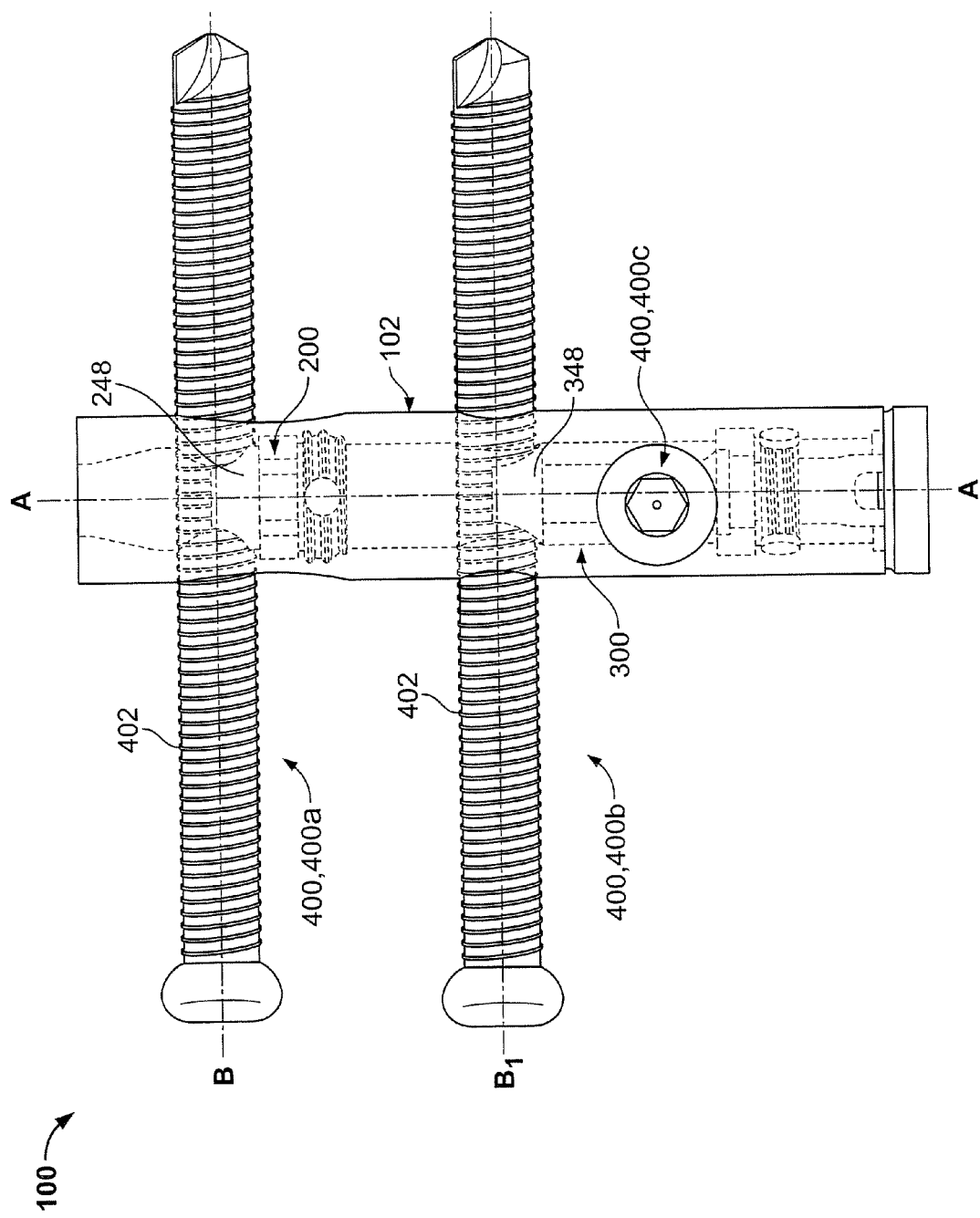
FIG. 5 is a perspective view of a detail of an intramedullary fixation device according to the present teachings, the fixation device shown with a compression device in a engaged position relative to a first fixation fastener, and with a locking device engaging a second fixation fastener.

Referring to FIG. 5, after tibio-talar compression is achieved as described above, the calcaneal fixation fasteners 400b, 400c can be inserted through the first and second apertures 112, 114 of the IM implant 102 and the corresponding apertures 346, 344 of the locking device 300, respectively. A driver adapted or sized for the locking device can be used to engage the driver engagement formation 304 of the first component 310 of the locking device 300 to lockingly couple the calcaneal fixation fasteners 400b, 400c in the IM implant 102. Additionally, talo-calcaneal compression can still be performed using the externally mounted compression nut 510, as discussed above.

The present teachings provide a versatile intramedullary fixation device that can be used for fracture reduction and/or arthrodesis applications. It will be appreciated that the use of two independent of each other compression and locking devices 200, 300, each of which is preassembled in the longitudinal bore 102 of the IM implant 102, affords the surgeon the ability to perform in-board or in situ compression independently from the locking cortical fixation screws or other fasteners to the IM implant 102.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An intramedullary fixation device comprising:
   an intramedullary implant having a longitudinal bore along a longitudinal axis, the longitudinal bore having a first internally threaded portion and a second internally threaded portion, the intramedullary implant including an elongated slot and first and second apertures transversely crossing the longitudinal axis;
   a two-component compression device preassembled in the longitudinal bore of the intramedullary implant, a first component of the compression device defining a first plurality of threads that engage the first internally threaded portion, the compression device movable along the longitudinal axis, a second component of the compression device defining an end opening aligned with the elongated slot of the intramedullary implant; and
   a two-component locking device preassembled in the longitudinal bore of the intramedullary implant, a first component of the locking device defining a second plurality of threads that engage the second internally threaded portion, a second component of the locking device including first and second openings aligned along the first and second apertures of the intramedullary implant.

2. The fixation device of claim 1, wherein the second component of the compression device is coupled to the first component of the compression device.

3. The fixation device of claim 2, wherein the first component of the compression device includes a resilient portion and a flange received in an internal groove of the second component of the compression device.

4. The fixation device of claim 3, wherein the second component of the locking device is coupled to the first component of the locking device.

5. The fixation device of claim 4, wherein the first component of the locking device includes a resilient portion and a flange received in an internal groove of the second component of the locking device.

6. The fixation device of claim 5, wherein the second component of the compression device has an outer periphery keyed to a first inner periphery of the longitudinal bore at a first location.

7. The fixation device of claim 6, wherein the second component of the locking device has an outer periphery keyed to a second inner periphery of the longitudinal bore at a second location.

8. The fixation device of claim 7, wherein the second inner periphery of the longitudinal bore in the second location is different than the first inner periphery of the longitudinal bore in the first location.

9. The fixation device of claim 8, wherein the first inner periphery is smaller than the second inner periphery.

10. The fixation device of claim 1, wherein the end opening of the compression device and the first and second openings of the locking device each include internal ridges for engaging corresponding threaded fixation fasteners.

11. An intramedullary fixation device comprising:
    an intramedullary implant having a longitudinal bore along a longitudinal axis, the intramedullary implant including an elongated slot and first and second apertures transversely crossing the longitudinal axis;
    a compression device preassembled in the longitudinal bore of the intramedullary implant, the compression device movable along the longitudinal axis, the compression device including a first component threadably coupled to the longitudinal bore of the intramedullary implant and a second component coupled to the first component, the second component having an end opening aligned with the elongated slot of the intramedullary implant; and
    a locking device preassembled in the longitudinal bore of the intramedullary implant, the locking device including a first component threadably coupled to the longitudinal bore of the intramedullary implant and a second component coupled to the first component, the second component including first and second openings aligned along the first and second apertures of the intramedullary implant,
    wherein the first component and the second component of the compression device are each separate from the first component and the second component of the locking device.

12. The fixation device of claim 11, wherein the end opening of the compression device is defined between first and second end extensions of the second component of the compression device.

13. The fixation device of claim 11, wherein one of the first and second openings of the locking device is defined between end extensions of the second component of the locking device.

14. The fixation device of claim 11, wherein each one of the end opening of the compression device and the first and second openings of the locking devices includes internal ridges for engaging threaded fixation fasteners received through the corresponding openings.

15. The fixation device of claim 11, wherein each one of the first components of the compression and locking devices includes a driver engagement formation.

16. The fixation device of claim 11, wherein each one of the compression and locking devices is cannulated along the longitudinal axis of the intramedullary implant.

17. The fixation device of claim 11, wherein the end opening of the compression device is substantially perpendicular to the longitudinal axis of the intramedullary implant and oriented in a lateral-medial direction.

18. The fixation device of claim 11, wherein the first and second openings of the locking device are substantially perpendicular to one another, and wherein one opening is oriented in a lateral-medial direction and the other opening is oriented in a posterior-anterior direction.

19. An intramedullary fixation device comprising:
    an intramedullary implant for ankle arthrodesis, the intramedullary implant having a longitudinal bore along a longitudinal axis, an elongated talar slot, a lateral-medial through-hole, and a posterior-anterior through-hole, the longitudinal bore defining a first internally threaded portion and a second internally threaded portion;

a two-component compression device preassembled in the longitudinal bore of the intramedullary implant, a first component of the compression device defining a first plurality of threads threadably engagable with the first internally threaded portion, a second component of the compression device defining an end opening corresponding to the elongated slot for receiving a talar fixation fastener transversely to the longitudinal axis of the intramedullary implant, the first component of the compression device movable relative to the longitudinal bore to move the talar fixation fastener along the elongated slot for tibio-talar compression; and a two-component locking device preassembled in the longitudinal bore of the intramedullary implant, a first component of the locking device defining a second plurality of threads threadably engagable with the second internally threaded portion, the second component of the locking device defining a through-hole corresponding to the posterior-anterior through-hole of the intramedullary implant for receiving a first calcaneal fixation fastener, the locking device defining an end opening corresponding to the lateral-medial through-hole of the intramedullary implant for receiving a second calcaneal fixation fastener, the first component of the locking device movable relative to the longitudinal bore and the compression device to lock the first and second calcaneal fasteners in the intramedullary implant.

20. The fixation device of claim 19, wherein each one of the end opening of the compression device, the through-hole of the locking device and the end opening of the locking device includes internal ridges for engaging the corresponding talar, first calcaneal and second calcaneal fixation fasteners.

21. The fixation device of claim 19 in combination with the talar fixation fastener and the first and second calcaneal fixation fasteners, wherein each of the fixation fasteners is substantially perpendicular to the longitudinal axis of the intramedullary implant, and wherein the talar and the second calcaneal fasteners are substantially parallel to one another and substantially perpendicular to the first calcaneal fastener.

* * * * *

UNITED STATES PATENT AND TRADEMARK OFFICE
CERTIFICATE OF CORRECTION

| | |
|---|---|
| PATENT NO. | : 8,157,802 B2 |
| APPLICATION NO. | : 12/117765 |
| DATED | : April 10, 2012 |
| INVENTOR(S) | : Timothy M. Elghazaly and Philip H. Frank |

It is certified that error appears in the above-identified patent and that said Letters Patent is hereby corrected as shown below:

Column 1, line 49 -- "The a locking" should be --The locking--.
Column 2, line 37 -- "a engaged" should be --an engaged--.
Column 2, line 40 -- After "view" insert --of--.
Column 2, line 53 -- "longing device" should be --locking device--.
Column 4, line 11 -- "depending ion" should be --depending on--.
Column 4, line 42 -- After "also" insert --have--.

Signed and Sealed this
Twenty-sixth Day of June, 2012

David J. Kappos
*Director of the United States Patent and Trademark Office*